United States Patent [19]

Khanna

[11] Patent Number: 5,434,052
[45] Date of Patent: Jul. 18, 1995

US005434052A

[54] COMPLEMENTATION ASSAY FOR DRUG SCREENING

[75] Inventor: Pyare Khanna, Fremont, Calif.

[73] Assignee: Microgenics Corporation, Concord, Calif.

[21] Appl. No.: 95,267

[22] Filed: Jul. 21, 1993

Related U.S. Application Data

[63] Continuation of Ser. No. 908,634, Jul. 1, 1992, abandoned, which is a continuation of Ser. No. 394,017, Aug. 15, 1989, abandoned.

[51] Int. Cl.⁶ ............... G01N 33/535; G01N 33/542; G01N 33/566
[52] U.S. Cl. .................................. 435/7.6; 435/7.2; 435/7.8; 435/7.9; 436/500; 436/501; 436/503; 436/537
[58] Field of Search ............... 435/7.2, 7.6, 7.8, 7.9, 435/7.1; 436/500, 501, 503, 537

[56] References Cited

U.S. PATENT DOCUMENTS

| | | | |
|---|---|---|---|
| 3,817,837 | 6/1974 | Rubenstein et al. | 435/7.9 |
| 4,134,792 | 1/1979 | Boguslaski et al. | 436/537 |
| 4,708,929 | 11/1987 | Henderson | 435/188 |
| 4,760,029 | 7/1988 | Barnett et al. | 436/504 |
| 4,786,591 | 11/1988 | Draeger et al. | 436/512 |
| 4,859,585 | 8/1989 | Sonnenschein et al. | 435/29 |
| 4,950,591 | 8/1990 | Cherskey | 435/7.2 |
| 4,997,771 | 3/1991 | Barnett et al. | |
| 5,328,830 | 7/1994 | Janis et al. | 435/7.8 |

FOREIGN PATENT DOCUMENTS

| | | |
|---|---|---|
| 042673 | 12/1981 | European Pat. Off. . |
| 069450 | 1/1983 | European Pat. Off. . |
| 310430 | 4/1989 | European Pat. Off. . |
| 327312 | 8/1989 | European Pat. Off. . |
| 2103363 | 2/1983 | United Kingdom . |
| WO86/02666 | 5/1986 | WIPO . |

*Primary Examiner*—David Saunders
*Attorney, Agent, or Firm*—Richard L. Neeley; Luann Cserr

[57] ABSTRACT

Compounds are evaluated for their binding to naturally occurring receptors, by employing the natural ligand conjugated to an enzyme donor fragment of β-galactosidase for competing with the sample compound for the natural acceptor binding site or in the absence of competition where the sample compound binds to an allosteric site. By adding the enzyme acceptor fragment of the β-galactosidase and substrate, the binding affinity of the sample compound may be evaluated as a measure of agonist or antagonist capability.

8 Claims, No Drawings

COMPLEMENTATION ASSAY FOR DRUG SCREENING

CROSS REFERENCE TO RELATED APPLICATIONS

This application is a continuation of U.S. application Ser. No. 07/908,634, filed Jul. 1, 1992, (now abandoned) which is a Continuation of U.S. application Ser. No. 07/394,017, filed 15 Aug. 1989, (now abandoned).

INTRODUCTION

1. Technical Field

The technical field of this invention is the measuring of the binding propensity of compounds to natural receptors.

2. Background

A large number of drugs are involved with binding to receptor compounds, where a signal may be transduced across a membrane, or the effective concentration of the drug is modulated by binding to a receptor, or the binding of a receptor to its ligand may be modulated allosterically, or the like. For the most part, there is no way today to define a spatial conformation and charge distribution which will be optimal for binding to a particular site. Therefore, much of drug design involves comparison with the naturally binding substance, as well as drugs which have been found to be effective where these exist, some molecule modeling, and any other physical or chemical insight which has been provided by various techniques. Still, despite the large amount of information which is available, drug design has many empirical aspects. After one has exhausted all of the insights for describing what a drug may look like, one is then frequently lead to synthesizing a variety of compounds and measuring their effectiveness. In addition, large numbers of compounds are produced which are never screened, because of the relatively high cost of the various assays. It is therefore of great interest to provide a technique which can identify compounds which have analogous binding affinities with the ligand, where the screening may be rapid, efficient and inexpensive.

Relevant Literature

See U.S. Pat. No. 4,708,929 and PCT/US/85-02095.

SUMMARY OF THE INVENTION

Compounds are screened for binding to naturally occurring proteinaceous receptors or subunits thereof by conjugating the natural ligand or cross reactive compound to an enzyme donor fragment of $\beta$-galactosidase. By providing for competition between the conjugate and the experimental compound for the receptor, or for the receptor binding to an allosteric site, the binding propensity of the experimental compound can be determined in relation to the enzyme activity obtained when enzyme acceptor is added to the assay medium.

DESCRIPTION OF SPECIFIC EMBODIMENTS

In accordance with the subject invention, it has now been found that the binding of an experimental compound to the binding site of a receptor or an allosteric site of a receptor can be measured by employing a conjugate of a ligand for the receptor binding site covalently bonded to the enzyme donor fragment of $\beta$-galactosidase. In contrast with antibody binding to a ligand conjugated to an enzyme donor fragment, it is found that receptors bind to the ligand of the conjugate in a manner analogous to the natural binding of the ligand to the receptor. Due to the high affinity and the significant number of contacts between the ligand the receptor, binding to the receptor appears to be different from binding of the ligand to an antibody.

In the case of the receptor, it would appear that the receptor inhibits enzyme activity either by preventing complex formation with enzyme acceptor or preventing the complex of enzyme donor and enzyme acceptor from being active. By contrast, antibody appears to slow down the rate of complex formation, so that by measuring an early rate, while complex formation is occurring, one can measure the amount of antibody bound to the ligand of the conjugate. Because of the natural binding of ligand to receptor, one can measure cross-reactivity of potential agonists or antagonists by measuring enzyme activity in a competition between the experimental compound and the conjugate.

There appears to be a difference in nature of the binding between a natural receptor and its haptenic ligand and an antibody and its haptenic ligand as the binding affects the activity of the enzyme donor of $\beta$-galactosidase in forming an active enzyme complex with the enzyme acceptor. The strength of the binding of the receptor to its haptenic ligand as well as the spatial relationship of the binding of the receptor to its haptenic ligand can be related to the activity of the enzyme donor. In this way the change in observed enzyme activity can be related to the nature of the binding of the haptenic ligand to the receptor.

In addition, one can measure allosteric effects, where the allosteric effect is to enhance or diminish the binding of the ligand to the receptor, by measuring the effect of the allosterically binding experimental compound on enzyme activity.

In carrying out the assay, the experimental compound, enzyme donor-ligand conjugate, ligand receptor, and any other reagents may be added in any order, except for the enzyme acceptor which will usually be added not earlier than there having been at least initiation of reaction with both the experimental compound and the enzyme donor ligand conjugate.

In a preferred embodiment the experimental compound is combined with the receptor in an appropriate buffered medium and the mixture allowed to incubate for sufficient time to at least substantially approach equilibrium. To the mixture is then added the conjugate of the ligand and enzyme donor, followed by an additional incubation at a predetermined temperature. After the second incubation, the enzyme acceptor reagent is added followed by a further incubation and the enzyme rate may then be determined.

In the preferred embodiment, the first step is the combination of the experimental compound and the receptor in a buffered medium. Usually, the concentration of the two components will be selected so as to allow for achieving equilibrium within a relatively short time, generally in the range of about 5 to 60 min, preferably about 5 to 30 min. The temperature may range from about 4° to 40° C., conveniently room temperature may be employed. The pH will generally be in the range of about 5 to 13, selecting a pH which is convenient for the reaction between the experimental compound and the binding compound. If desired, an aliquot of the first solution may be employed.

In the next step, the solution prepared above is combined with the conjugate solution. The conjugate solution will generally have conjugate at a concentration which will vary with the binding affinity of the receptor. Thus, concentrations may range from 1 pM to about 1 µM. Conveniently, the conjugate solution may also include a substrate for β-galactosidase to avoid additional steps. Alternatively, the substrate could be included with the enzyme acceptor reagent. The enzyme donor conjugate solution will generally be buffered in a pH in the range of about 5 to 9, usually 6.5 to 7.5. Other additives may include chelating agents, e.g., ethylene glycol tetraacetic acid, stabilizers, such as sodium azide and dithiothreitol, and nonionic detergents. The buffer will be sufficient to maintain buffering capability in the assay medium, generally ranging from about 50 to 500 mM. The chelating agent and azide will generally range from about 5 to 50 mM, while the detergent will be present in about 0.01 to 0.1% and the dithiothreitol from about 0.01 to 0.1 mM.

Usually, the amount of the first solution will be substantially smaller than the amount of the enzyme donor conjugate reagent solution, so that the buffering in the enzyme donor conjugate reagent solution will control the pH. Thus, the volume ratio will generally be from about 1:1-5.

The receptor will normally be used as a reagent solution, when it is added to the experimental compound sample solution. For the most part, the receptor will be employed as a buffered solution at a pH in the range of about 5 to 9, where the buffer will generally range from about 50 to 500 mM and other compounds may be added for stability. Thus, from 0.1 to 2% of an inert protein, such as serum albumin, from about 0.1 to 2% of detergent, such as Lubrol, and from about 5 to 50 mM sodium azide may be present. The various materials which are employed will vary to some degree, depending upon the nature of the receptor.

The combined solution comprising the sample, receptor, and enzyme donor conjugate may be incubated for a short time, generally from about 1 to 10 min, more usually from about 2 to 5 min, desirably at physiologic temperature, although any temperature may be used from about 4° to 40° C. Preferably, the temperature will be in the range from about 25° to 37° C., more preferably 37° C. To the solution may then be added the enzyme acceptor and the mixture allowed to incubate for a sufficient time, generally from about 1 to 30 min, more usually from about 2 to 15 min, primarily depending upon the binding affinity of the receptor, its size, concentration of the various components in the solution, the temperature, and the like. Again, any temperature may be used, preferably from about 25° to 37° C., more preferably about 37° C.

The total volume of the sample will generally range from about 50 to 500 µl, where desirably the major dilution will occur with the addition of the enzyme acceptor. This allows for more rapid reaction between the receptor and the sample compound and conjugate, since their concentrations will be higher during the competition. Since large amounts of enzyme acceptor may be employed, the dilution by the enzyme acceptor need not have a significant effect on the rate of complex formation between the enzyme donor and the enzyme acceptor. Thus, the volume ratio of the enzyme acceptor solution to the prior mixture will generally be from about 1 to 5:1, more usually from about 1.5-3:1.

After sufficient time for the enzyme complex to form, the rate of enzymatic activity in the assay medium may be determined in accordance with conventional ways. By employing appropriate substrates which provide for a product having strong absorption in the ultraviolet or visible region, preferably the visible region, the rate of change of absorption may be read in a spectrophotometer.

The subject protocol is particularly applicable with automated instrumentation, where the various mixtures may be added to the sample and incubated automatically followed by introducing the reaction mixture or aliquot thereof into the light beam path for the rate determination. Thus, a large number of samples may be rapidly screened where the same reagents may be employed for evaluating sample compounds which bind to the same receptor.

A large number of compounds are known to bind to protein receptors, where there is an interest in being able to evaluate the binding affinity of the compounds. For the most part, the compounds will be small organic molecules, having a molecular weight below about 5 kDal, usually below about 2 kDal. Where the ligand for the receptor is substantially larger than 5 kDal, to the extent that a much smaller sequence is known which can substantially mimic the large ligand, that sequence may serve in its place. For example, the oligopeptide which binds to such receptors as the insulin receptor, are known and may serve in place of insulin to determine the binding affinity of other compounds for their respective receptors.

The receptor may be a pure composition, isolated from a naturally occurring source, may be prepared by genetic engineering techniques, may be a crude cell lysate, membrane fragment, or may be partially purified. The receptor will be used in a form which does not interfere with the purpose of the assay.

Receptors may be membrane protein receptors, particularly the plasmalemma which include G proteins, CD proteins, neurotransmitter receptors, growth factor receptors, steroid receptors, growth factor receptors, Vitamin D receptors, cytokin receptors, etc., blood protein receptors, such as polyiodothyronine receptors, cholesterol receptors, etc., or other receptors associated with individual organs, such as muscle, skin, intestine, heart, CNS, pancreas, etc. The receptors may be used as a soluble protein, in a membrane fragment, or may be modified to make an insoluble protein soluble, e.g., remove a transmembrane integration sequence. Among ligands and receptors are folate and folate binding protein, thyroxine or triiodothyroine and thyroxine binding globulin, B12 and intrinsic factor, cholesterol and low density lipoprotein, glucocorticoids and glucocorticoid binding protein, acetylcholine and the acetylcholine receptor.

For the most part, the region of binding of these compounds to their receptors are known or can be readily determined by preparing a few derivatives. In any event, an available functional group present on the ligand may be employed or a functional group introduced. The literature is repleat with conjugates of ligands to other compounds, where the conjugates have been used as reagents for formation of antibodies, as reagents in assays, or for other purposes. Where the conjugate has been used for binding to its natural receptor, this conjugate will usually suffice.

A wide variety of functional groups may be employed for linking the ligand to the enzyme donor fragment. The linkages may be between a thiol and an activated olefin, a peptide bond, where the carboxy will usually be present on the ligand, reductive amination, or the like. Methods for preparing the enzyme donor conjugate are amply described in U.S. Pat. No. 4,708,929. For the most part, the conjugate will be formed at a cysteine or lysine, which may be naturally present or introduced into the enzyme donor fragment.

For the most part, the natural sequence of the β-galactosidase donor fragment which is employed will be subject to one or more substitutions for the introduction of a cysteine or lysine. The basic sequence which will be referred to is as follows:

```
1        * 5            10          15
M D P  S G N P  Y G I  D P T  Q S
       20       * 25*              30
S P G  N I  D P R A S  S N S  L A
                               6
       35         * 40   *        45
V V L  Q R R D W E N  P G V T  Q
                       20
       * 50    *       55           60
L N R  L A A H P P  F A S W R  N
              30
*      65    * 70              75
S E E  A R T D R P  S Q Q  L R S
40                       50
       80           85 *    89
L N G  L E S R S A G M P L G
56
```

Numbers underneath letters indicate the
wild-type β-galactosidase numbering.
*Indicates amino acid substitutions to C or K.

Preferred regions for substitutions include the region from about amino acid 20 to amino acid 30; from amino acid 35 to amino acid 45; from amino acid 60 to amino acid 89. Where more than one substitution is employed, it is preferred the substitutions be separated by at least about 5 amino acids, preferably at least about 10 amino acids, and more preferably from about 20 to 60 amino acids. Preferably, the region from about amino acids 48 to 61 is not used for substitution, although the particular site for substitution will to a significant degree depend upon the nature of the conjugate. Thus, one site may be favored over another site when preparing one conjugate as compared to another conjugate.

Sites of particular interest include amino acids 4, 23, 25, 39, 42, 45, 68 and 86. Regions for deletion include the region from amino acids 1 to 20, particularly 5 to 20, or any sequence therein. Regions of interest for substitution of other than a conjugation site include the region from about 70 to 85, particularly from about 72 to 80, more particularly 74 to 77, where a greater or lesser number of amino acids may be introduced, where the substitutions may be conservative or non-conservative. By conservative is intended having the same or substantially the same charge type and general conformation, for example, neutral amino acids may be substituted for other neutral amino acids, aromatic amino acids for other aromatic amino acids, charged amino acids for other charged amino acids of the same charge type, and the like. Furthermore, one could consider for conservative changes, retaining a hydrophobic region as compared to a hydrophilic region, where non-conservative would be to change the nature of the region from hydrophilic to hydrophobic or vice versa.

A large number of linking groups may be employed for joining a wide variety of specific binding pair members to a functionality present in the ED. As already indicated, for the most part, the functionality present on the ED for linking will be a mercaptan or amino group. For mercaptans, of particular interest are a wide variety of readily available reagents, involving activated halogen, activated olefin, or mercapto, where the first two form thioethers and the second a disulfide. Specific compounds include N-maleimidobenzoic acid, α-bromoacetamidocyclohexanecarboxylic acid, N-maleimidosuccinic acid, methyldithioacetic acid, etc. For amino groups, a wide variety of active halogens or carboxylic acid groups may be employed, particularly activated carboxylic acid groups, where the carboxylic acid groups may be activated with carbodiimide, active esters, such as N-hydroxy succinimide, o-nitrophenol, p-nitrophenol, etc. The procedures for conjugation are well known in the literature and are amply illustrated by U.S. Pat. Nos. 3,817,837; 4,262,089; 4,233,401; 4,220,722 and 4,374,925.

The linking group may merely be a bond, for example where the ligand has a carboxylic acid group which can be activated to react with the amino group of ED or may be of one or more atoms other than hydrogen, usually from about 1 to 24 atoms, more usually from about 1 to 12 atoms. Besides carbon atoms, the atoms in the chain may include nitrogen, sulfur, oxygen or the like.

Besides conjugation through a chemical reaction, one can provide for a fused protein by preparing a nucleic acid sequence encoding the ED joined to an amino acid sequence which is immunologically cross-reactive with a peptide of interest. One can synthesize appropriate strands of deoxynucleotides which provide for a fusion protein of the epitope(s) of interest with the ED, where the epitope(s) of interest may be at the N- or C- terminus of the ED, preferably the N-terminus.

The fusion protein may be of any size, usually being not greater than about 500 amino acids, more usually being not greater than about 200 amino acids, and preferably not greater than about 150 amino acids, including the ED sequence.

Enzyme Acceptors

The enzyme acceptor may be naturally occurring or synthetic. By synthetic is intended the use of recombinant DNA techniques to provide for the desired amino acid sequence. For the most part, the sequence of M13 will be employed as the basic sequence for the enzyme acceptor (EA). Of particular interest is the reduction in the number of available sulfhydryl groups present in the sequence. The EA M15 appears to have 5 cysteine residues available on the surface. Preferred EAs have fewer than 5, preferably fewer than 3 exposed cysteine residues, as a result of substitutions of the cysteine, particularly conservative substitutions, such as G, A, M, S, T, etc.

Method of Preparation

The subject polypeptide sequences may be prepared by any convenient means. Thus, the sequences may be synthesized on commercially available synthesizers. However, where the sequence is to be greater than about 50 amino acids, the efficiency of synthesis drops, so that other methods may become more attractive. One of the alternative methods is the use of recombinant technology, where single strand deoxynucleotide sequences are prepared encoding portions of the sequence of interest or sequence complementary thereto. The strands are for the most part overlapping, so that when hybridized and ligated, the resulting double stranded DNA sequence encodes the desired amino acid sequence. The sequence may then be inserted in any convenient expression vector.

A large number of expression vectors are commercially available or have been described in the literature. While for the most part prokaryotic hosts will be employed, in some instances eukaryotic hosts will be desirable, particularly where there are fusion proteins and it is desired that the fusion protein be processed. The vector will normally comprise the coding sequence, 5' in the direction of transcription to the coding sequence, a transcriptional initiation regulatory region or promoter, and 3' to the coding region in the direction of transcription, a transcription and translation termination regulatory region, so as to provide an expression cassette. Particularly, for transformation into prokaryotes, there will be a replication system which is functional in the host and provides for stable maintenance of the vector.

A wide variety of replication systems have been identified and used in prokaryotes, as well as eukaryotes. Also, there will normally be a marker for selection of those host cells which have been transformed with the vector. For the most part, the marker will be resistance to a toxin, e.g., an antibiotic, or provide for complementation of an auxotrophic host to provide prototrophy.

Transformation may be achieved by transfection, using a viral vector, protoplast fusion, transformation using calcium precipitated DNA, or other convenient technique. The manners of transformation are conventional and may be found in Maniatis et al, *Molecular Cloning: a Laboratory Manual*, Coldspring Harbor Laboratory, Coldspring Harbor, N.Y. 1982.

If desired, the sequence may include a signal sequence for secretion of the polypeptide product from the host. A wide variety of signal sequences are available, particularly for eukaryotic organisms. Where a signal sequence is not employed, it will be necessary to lyse the cells in order to extract the desired polypeptide.

The transformed host cells may be grown in an appropriate medium for sufficient time for the desired polypeptide to be formed and the product isolated, the manner depending upon whether the product was secreted or retained in the cytoplasm. Once the product is isolated, it may be purified in conventional ways, by chromatography, electrophoresis, gradient density separation, or the like.

The enzyme acceptor may be prepared in the same way or may be isolated from the host that produces the M15 sequence naturally. The particular manner in which the enzyme acceptor is produced is not critical to this invention.

Once the fragments are obtained, they may be modified as previously described. In the case of the enzyme acceptor, sulfhydryl groups may be capped or otherwise modified as appropriate. A linking group may be introduced onto the polypeptide or the polypeptide may be otherwise modified for reaction with the specific binding pair member portion of the conjugate. The polypeptide may then be combined with the specific binding pair member or analog thereof, and reacted in accordance with the nature of the functional groups and the conditions required for the reaction. For the most part, aqueous media will be used under mild conditions, usually under about 60° C., preferably under about 40° C.

An enzyme substrate is employed that when cleaved by the enzyme results in a change in the amount of light absorbance (optical density) or emission of the assay medium. That is, cleavage of the substrate results in the appearance or disappearance of a colored or fluorescent product. Preferred enzyme substrates include o-nitrophenyl galactoside (ONPG) and chlorophenol red-$\beta$-galactoside (CPRG). ONPG, CPRG and other comparable enzyme substrates are commercially available. ONPG will generally be used in a concentration of from about 0.5 to 2.0 mg/ml. Other substrates will be used in concentrations to provide a comparable signal to ONPG.

The following examples are offered by way of illustration and not by way of limitation.

EXPERIMENTAL

EXAMPLE 1

A. Preparation of B12-ED4 Conjugate a) Preparation of Activated B12 Derivative

A solution of 1.18 mg of cyanocobalamin-e-N-propylamine (prepared from the corresponding carboxylic acid J. F. Kolhouse and R. H. Allen, J. Clin. Invest., 1977, 60, 1381) is dissolved in 0.1 ml of 50 mM sodium phosphate, pH=7.3 buffer. A solution of 2.2 mg sulfosuccinimidyl 4-(N-maleimidomethyl)cyclohexane-1-carboxylate (SMCC) (Pierce Chemical Company) in 0.1 ml of buffer was then added. The solution was vortexed and left to stand at room temperature for thirty min. The crude reaction mixture was injected onto an analytical $\mu$ Bondapak Phenyl HPLC column (Waters Associates). The proper fractions were combined, frozen at $-70°$ C. and lyophilized.

b) Preparation of ED4-B12 Conjugate

About 0.25 part of the lyophilized product from the previous preparation was dissolved in 200 $\mu$L of 50 mM sodium phosphate, pH=7.3. A solution of 1.1 mg of ED4 (referred to as H6 in PCT/US/85-02095) in 200 $\mu$L of 50 mM sodium phosphate, pH=7.3, was added to the Vitamin B12 derivative solution, the resulting solution mixed thoroughly, and the reaction solution allowed to stand for one hour at room temperature. HPLC purification on a Waters $\mu$ Bondapak Phenyl column afforded pure ED4-Vitamin B12-C3-SMCC. The proper fractions were identified by bioassay and absorbance at 360 nm. These fractions were frozen, lyophilized and stored at $-70°$ C.

B. Inhibition of ED4-B12 Conjugate with Intrinsic Factor (Receptor)

The following reagents are prepared:

Binding Protein Receptor Reagent consists of Porcine Intrinsic Factor (0.5 mg/ml, Scripps Laboratories, San Diego) diluted approximately 1:2000 in 150 mM potassium phosphate, 50 mM sodium borate, 1% BSA (B12 Grade BSA, Sigma), 1% Lubrol and 20 mM sodium azide, pH 7.0.

ED4-B12 Conjugate/Substrate Reagent contains approximately 450 pM ED4-B12, 2.0 mg/ml CPRG chlorophenol red-$\beta$-D-galactopyranoside (Boehringer Mannheim), 100 mM sodium phosphate, 150 mM potassium phosphate, 10 mM ethylene glycol tetraacetic acid, 20 mM sodium azide, 0.05% Tween 20 with 0.05 mM dithiothreitol, pH7.0.

EA Reagent consists of a recombinant protein resembling the carboxyl-terminal end of $\beta$-galactosidase (see PCT/US/85-0295 EA22) in 100 mM sodium phosphate, 150 mM potassium phosphate, 10 mM ethylene glycol tetraacetic acid, 5 mM magnesium acetate 20 mM sodium azide, 0.05% Tween 20 with 0.05 mM dithiothreitol pH 7.0. EA concentration is approximately 9.0 µM.

The assay procedure involves mixing 300 µl of B12 sample with 100 µl of pH 12.7 300 mM sodium carbonate and 100 µl of binding protein reagent. This solution is incubated for >15 min at room temperature. This is the pretreated sample. An instrument (Clinical Chemistry analyzer) is programmed to deliver 30 µl of pretreated sample with 100 µl of ED-B12/substrate reagent. This is incubated for 2 to 5 min at 37° C. This is followed by the addition of 50 µl of EA reagent to the reaction mixture by the instrument and is incubated for 11 min at 37° C. The enzyme rate is read by absorbance change at 570 nm for 1 to 4 min. The following table indicates a typical assay performance.

| Amount of B12 Sample (pg/ml) | Observed Enzyme Rate | % Inhibition of Enzyme Conjugate |
| --- | --- | --- |
| 0 | 52.6 | — |
| 2,000 | 106.9 | 50.8 |
| 20,000 | 121.4 | 56.7 |

More Complete inhibition can be achieved when Binding Protein Reagent is more concentrated (i.e., 1:400 or 500 dilution of Scripp Labs IF):

| O B12 | 17.8 Rate | — |
| --- | --- | --- |
| ∞ B12 | 154.2 Rate | 89.7% |

Protocol used 55 µl BP Reagent, 200 µl ED/Substrate, 60 µl EA Reagent.

EXAMPLE 2

A. Preparation of ED4-T4 Conjugate
The conjugate is described in PCT/US/02095, designated as H6-T4.
B. Inhibition of ED4-T4 Conjugate by Thyroxin Binding Protein Receptor
The following reagents were employed:
EA Reagent/Buffer
  Buffer=20 mM NaPO4 10 mM EGTA, 2 mM MgOAc, 3.6% Glycerol, 5 mM Sucrose, 20 mM NaN3, pH 7.0
  Reagent=5U EA/Test or 31.25 U/ml of EA in EA Buffer
ED Reagent/Buffer
  Buffer=20 mM NaPO4, 10 mM EGTA, 6.25 mg/ml ONPG, 0.05% Tween/DTT, 20 mM NaN3, pH 7.0
  Reagent=18 nM ED4-T4 system concentration or 112.5 nM ED4-T4 in ED reagent buffer

| Machine Program Parameters: | | | |
| --- | --- | --- | --- |
| Wavelength: | 420 nM | EA Reagent R1: | 160 µl |
| Read Time: | 3–4 min rate | ED Reagent R2: | 40 µl |
| Delay Between R1 and R2: | 50 sec | Sample: | 20 µl |
| | | H2O: | 30 µl |
| Temperature: | 37° C. | Total Assay Volume: | 250 µl |

Receptor Description
The receptor was purified TBG from Protus Laboratories, South San Francisco, CA diluted in PBS.

Data
The following table shows the % Inhibition of ED-T4 conjugate by thyroxin binding globulin.

| Conc (µg/ml) of TBG Receptor | Observed Enzyme Rate (mA/min) | % Inhibition |
| --- | --- | --- |
| 0 | 471 | 0% |
| 18.3 | 367 | 22% |
| 55.0 | 154 | 68% |

EXAMPLE 3

A. Preparation of ED4-Folate Conjugate
Folic acid (10.0 mg), dicyclohexylcarbodiimide (DCC, 4.6 mg) and N-hydroxysuccinimide (NHS, 2.8 mg) were dissolved in a 1.5 mL Eppendorf tube in freshly distilled dimethylformamide (1.0 mL) with warming and stirred at room temperature for 2 h. Nearly all of the folic acid dissolved. The mixture was microfuged and the supernatant (200 µL) was added to ED14 (400 µg) in 0.2M borate, pH 7.8 (600 µL), and dimethyl-formamide (150 µL). The mixture was gently stirred for 1 h, then microfuged in an Eppendorf tube. The supernatant was loaded on a 10 mL G-25 column (Pharmacia) that had been pre-equilibrated with 20 mM TRIS, pH=8.5, and eluted with 20 mM TRIS, pH=8.5. The complementing fractions were combined and purified by ion exchange chromatography. Column: Pharmacia Q Sepharose 5×50 mM. Eluents: A) 20 mM TRIS, pH=8.5; B) A+3.5M NaCl. Gradient: 0–100% in 40 min. Flow Rate: 1.0 mL/min. Detection: 280 nM. The fraction eluting at approximately 29 m(?) was found to have 95% Inhibition. The fractions containing the product were stored at 70° C.

B. Inhibition of ED14-Folate Conjugate with Folate Binding Protein (Receptor)
The following reagents are prepared:
Binding Protein Reagent consists of bovine Folate Binding Protein (Biochemical Inc., Englewood, Colo.) diluted approximately 1:2500 in 150 mM potassium phosphate, 50 mM sodium borate, 1% BSA (B12-Grade BSA, Sigma, St. Louis, Mo.), 1% Lubrol and 20 mM sodium azide, pH 7.0.

ED14-Folate Conjugate/Substrate Reagent contains approximately 6.3 nM ED-Folate, 1.0 mg/ml OCNPG (o-chloro-p-nitrophenol galactopyranoside), 100 mM sodium phosphate, 150 mM potassium phosphate, 10 mM ethylene glycol tetraacetic acid, 2.5 mM dithiothreitol, 20 mM sodium azide, 0.05% Tween 20 with 0.05 mM dithiothreitol, pH 7.0.

EA Reagent consists of a recombinant protein resembling the carboxyl-terminal end of β-galactosidase in 100 mM sodium phosphate, 150 mM potassium phosphate, 10 mM ethylene glycol tetraacetic acid, 5 mM magnesium acetate, 20 mM sodium azide, 0.05% Tween 20 with 0.05 mM dithiothreitol pH 7.0. EA concentration is approximately 2.2 µM.

The assay procedure involves mixing of 300 µl of folic acid sample with 100 µl of binding protein reagent and incubation for 15 min at room temperature. This becomes the pretreated sample. An instrument (clinical chemistry analyzer) is programmed to deliver 30 µl of pretreated sample with 100 µl of ED-Folate reagent for 2 to 5 min at 37° C. This is followed by the addition of 220 µl of EA reagent to the reaction mixture by the instrument and the enzyme rate is read by absorbance change at 405 mM. The following table indicates a typical assay performance.

| Amount of Folate in Sample (g/mL) | Observed Enzyme Rate | % Inhibition of ED14-Folate Conjugate |
|---|---|---|
| 0 | 117 | 67.2% |
| 20 | 290 | 18.8% |
| 200 | 357 | 0.0% |

It is evident from the above results, that the subject method provides for a rapid and convenient means for screening a wide variety of compounds for binding to natural receptors, either at the binding site, or at the allosteric binding site for determining binding affinity. The assay can be automated, so that large numbers of compounds may be screened in a rapid and efficient manner under comparable conditions, so as to provide for a reproducible and exact comparisons. Due to the binding of the receptor to the conjugate which substantially mimics the natural binding of the receptor to its ligand, an accurate comparison can be made between the binding of a sample compound and the binding of the normal ligand. This relationship can be easily determined by a simple determination of enzyme activity.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for evaluating the effect of a compound on the ability of a natural receptor to bind its natural ligand comprising:
    combining in an assay medium said natural receptor and said compound for a sufficient time for said compound to bind to an allosteric binding site of said receptor;
    adding to said assay medium an enzyme donor conjugate comprising an enzyme donor fragment linked to said natural ligand, or to a moiety capable of mimicking the binding of said ligand to said natural receptor, for a sufficient time for said conjugate to bind to available receptor, said enzyme donor conjugate being able to form a holoenzyme with a β-galactosidase enzyme acceptor fragment;
    adding said β-galactosidase enzyme acceptor fragment to said medium to form said holoenzyme with the portion of said conjugate remaining unbound to receptor; and
    determining the enzyme activity of said medium as a measure of the effect of said compound on the binding of said ligand to said receptor.

2. A method according to claim 1, wherein said ligand is a hapten.

3. A method according to claim 1, wherein said receptor is a surface membrane receptor.

4. A method according to claim 1, wherein said receptor is present as a cell lysate.

5. A method according to claim 1 wherein said combining is carried out at a temperature in the range of ambient temperature to 40° C., with said assay medium in a pH range of about 5 to 13 and with a compound binding time of about 5 to 30 minutes.

6. A method according to claim 5 wherein said temperature range is about 25° to 40° C.

7. A method according to claim 6 wherein said ligand is selected from the group consisting of thyroxine, folate and vitamin B-12.

8. A method for screening a plurality of test compounds for the ability of the test compounds to affect the ability of a natural receptor to bind its natural ligand comprising:
    combining in separate assay media one of each of said test compounds and said natural receptor for a sufficient time for said test compound to bind to an allosteric binding site of said receptor;
    adding to each assay medium an enzyme donor conjugate comprising an enzyme donor fragment linked to said natural ligand or to a moiety capable of mimicking the binding of said ligand to said natural receptor for sufficient time for said conjugate to bind to available receptor, said enzyme donor conjugate being able to form a holoenzyme with a β-galactosidase enzyme acceptor fragment;
    adding to each assay medium a β-galactosidase enzyme acceptor fragment to form said holoenzyme with the portion of said conjugate remaining unbound to receptor; and
    determining the effect of each of said test compounds on the ability of the receptor to bind natural ligand by determining the enzyme activity of each of said media as a measure of the effect of each of said test compounds on the binding of said ligand to said receptor.

* * * * *